| United States Patent [19] | [11] Patent Number: 4,961,735 |
|---|---|
| Siciliano | [45] Date of Patent: Oct. 9, 1990 |

[54] METHOD FOR DRAINING AND DRYING BODY FLUIDS

[75] Inventor: Anthony A. Siciliano, Ardsley, N.Y.

[73] Assignee: Evaporating Apparel Industries, Saddle River, N.J.

[21] Appl. No.: 188,435

[22] Filed: Apr. 29, 1988

[51] Int. Cl.[5] .................... A61F 13/16; A61L 15/00
[52] U.S. Cl. .................... 604/378; 604/371; 128/156
[58] Field of Search ............. 128/155, 156; 604/371, 604/378, 384

[56] References Cited

U.S. PATENT DOCUMENTS

| RE 28,674 | 1/1976 | Guyette | 604/371 |
|---|---|---|---|
| 2,254,883 | 9/1941 | Boyle | 128/156 |
| 2,841,529 | 7/1958 | Schmidt et al. | 128/155 |
| 3,063,452 | 11/1962 | Guercio | 604/378 |
| 3,561,441 | 2/1971 | Lombardi | 128/156 |
| 3,654,929 | 4/1972 | Nilsson et al. | 604/378 |
| 3,658,065 | 4/1972 | Hirsch | 128/156 |
| 3,709,221 | 1/1973 | Riely | 128/156 |
| 3,811,445 | 5/1974 | Dostal | 604/384 |
| 3,930,498 | 1/1976 | Monnet et al. | 128/156 |
| 3,976,075 | 8/1976 | Chinai et al. | 604/371 |
| 4,072,150 | 2/1978 | Glassman | 604/378 |
| 4,214,582 | 7/1980 | Patel | 128/156 |
| 4,414,268 | 11/1983 | Baldwin | 604/356 |
| 4,502,156 | 3/1985 | Wishman | 604/378 |
| 4,714,466 | 12/1987 | Dohzono et al. | 604/378 |

Primary Examiner—Stephen C. Pellegrino
Assistant Examiner—Sharon Rose
Attorney, Agent, or Firm—Thomas A. Beck

[57] ABSTRACT

A method of using an evaporating bandage which will drain and dry harmful body fluids from surgical incisions, wounds and burns and eliminate the problems associated therewith is disclosed. The bandage has a first layer made of an absorbent material and a second layer made of a non-absorbent material.

9 Claims, 1 Drawing Sheet

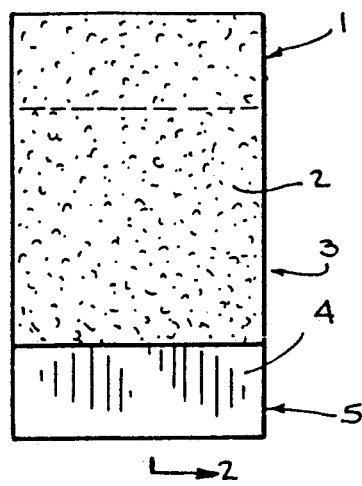
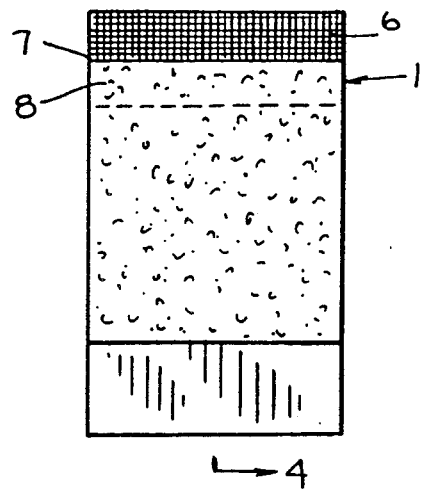
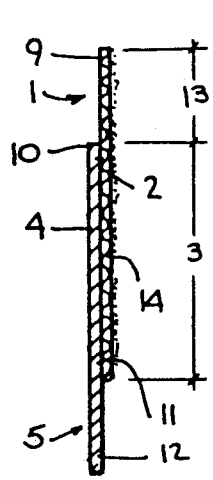
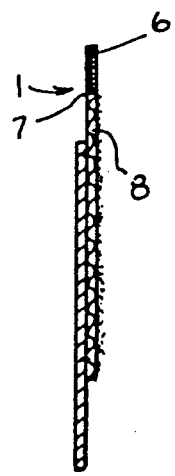
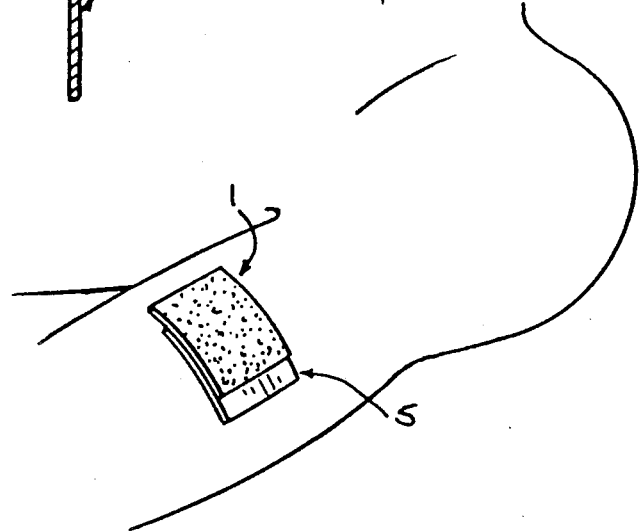

METHOD FOR DRAINING AND DRYING BODY FLUIDS

BACKGROUND OF THE INVENTION

The present invention relates to an article comprising a bandage which absorbs, drains, controls and evaporates body fluids which emanate from surgical incisions, wounds and burns, thereby eliminating certain problems associated therewith.

One of the problems associated with certain surgical procedures on a person, or the treatment of burns sustained by a person, is the control of body fluids which result therefrom. For example, after major surgery, in many instances there is external bleeding which occurs at the wound or incision. The blood flowing from the open source is really a tissue made up of a liquid material containing about 50% by volume of white cells and red cells and platelets. The other half of the volume of blood is made up of a fluid called plasma. In addition to blood emanating from the source, inflammation may set in during the course of healing of the wound or incision whereupon white blood cells are chemically attracted to the damaged area. When large numbers of white cells engulf bacteria and dying cells, they themselves die. In the case of a serious local inflammation in the vicinity of a wound or incision, the dead cells accumulate as pus and ooze from the wound or incision t outside of the body.

In the instance of a burn over a portion of the body, the fluid generated as a result of the burn oozes from the burn site.

Many of the current gauze bandages and gauze surgical dressings in use today only absorb the fluids from the injured skin area. Thus, body fluids that soak into these current bandages remain in the gauze fabric. When the bandage is saturated, it must be changed because retention of the fluids in the gauze bandage, in contact with the incision, wound or burn, can lead to serious infection. Furthermore, the presence of the aforementioned fluids in contact with the injured skin delays the healing process.

As a consequence, current gauze bandages are changed frequently. The procedure involved in changing a bandage saturated with body fluids during the healing process may reverse to some degree whatever healing that has taken place.

SUMMARY OF THE INVENTION

The article of the present invention is a bandage which is adapted to be applied to cover an area on the body which contains an incision, wound or burn to absorb the fluids which emanate therefrom. The bandage article of the present invention, which for the sake of convenience is referred to herein as "an evaporating bandage," drains, contains, evaporates and dries potentially harmful fluids which emanate from injured skin from two to five times faster than current gauze bandaging. This unexpected benefit in evaporation and drying is a result of the bandage construction which consists of a staggered layering of an absorbent material over a nonabsorbent material.

BRIEF DESCRIPTION OF THE DRAWINGS

While the specification concludes with claims particularly pointing out and distinctly claiming the subject matter of the invention, it is believed the invention will be better understood from the following description taken in conjunction with the accompanying drawings, wherein:

FIG. 1 illustrates a front view of one embodiment of the bandage;

FIG. 2 shows a cross sectional view of the bandage of FIG. 1 in place on the body;

FIG. 3 illustrates a front view of another embodiment of the bandage;

FIG. 4 shows a cross sectional view of the bandage of FIG. 3; and

FIG. 5 shows the bandage in place on the body.

The bandage configuration of the present invention comprises the three sections depicted in FIG. 1.

Top section 1 which is applied to, and is in direct contact with, the injured portion of the skin is comprised entirely of an absorbent material 2 capable of being sterilized. It absorbs the fluids oozing from the wound or burn. Absorbent material 2 is preferably fabricated from a terry cloth, i.e., a cotton material which contains a looped pile construction. Further, the preferred actual construction of the top section 1 is the absorbent material 2 comprising a terry pile surface on one side (i.e., the side facing the source of the body fluid) and a ribbed or plain knit surface on the other. In addition, the absorbent material may comprise wool.

Mid-section 3 comprises a continuation of the absorbent material 2 in overlapping contact with a layer of nonabsorbent material 4 which is located directly adjacent to and beneath absorbent material 2. Referring then to FIG. 2, it can be seen that there are two distinct layers of different materials, one atop the other, which comprise mid-section 3. Bottom section 5 of the bandage consists of a continuation of the nonabsorbent material 4 extending beyond the bottom edge of the absorbent material 2. The non-absorbent material may comprise polyamide which embodies the various nylon materials available.

The present invention relates to the use of the bandage described above, more specifically, it relates to a method of containing fluids emanating from the human body using said evaporative bandage, which method comprises contacting the location on the body from which said fluids are emanating with the bandage as depicted in FIGS. 1 and 2, said bandage comprising a first layer (1) made of a moisture-absorbent material (2) and a second layer (4) made of a non-moisture absorbent material; said first and second layers having top (9, 10) and bottom (11, 12) edge portions which are aligned and secured in staggered positions relative to each other so that at one end, said first layer top edge portion (9) extends beyond the second layer top edge portion (10) thereof and is in contact at area (13) with the location o the body from which said fluids are emanating, and, correspondingly, said second layer bottom edge portion (12) extends beyond the said first bottom edge portion (11) at the other end thereof, there being a resulting area (14) not in contact with the area from which said body fluids are emanating, wherein the portion of the surface of the lower portion of said first layer is in direct contact with a portion of the surface of the upper portion of said second layer.

Alternatively, as depicted in FIG. 3, top section 1 can be comprised of swatches of different absorbable materials. For example, top section 1 can comprise a section made of a gauze material 6, which is secured at 7 at its edge to a terry cloth portion 8. The gauze section can be secured to the terry cloth section along the respective edges by any suitable means. The evaporating bandaging of the present invention is applied with top section 1 covering and in direct contact with the injured skin.

Referring to FIG. 4, it can be seen that section 1 comprises gauze section 6 which has its lower edge in contiguous fixed relationship with the upper edge of terry cloth portion 7. Directly beneath section 1 is midsection 3 and bottom section 5 which are made of a nonabsorbable material.

The evaporating bandage must be applied to the wound or burn area in such a manner that the bandage sections 1, 3 and 5 will drape over the body and point downward as much as possible toward the ground. This allows the effect of gravity to influence migration of the body fluids flowing onto the evaporating bandage The capillary action of the body fluids collected, absorbed and retained in the absorbent material of the evaporating bandage, in conjunction with the force of gravity, draws the fluids down from section 1 into section 3. Since section 3 has an adjacent layer of a nonabsorbent material, there is a resistance to absorption from behind section 3. Since the bottom of section 3 borders on the non-absorbing material of section 5, absorption is also resisted from below section 3. This dual resistance of absorption from both behind and below creates a reservoir like effect in section 3.

Fluids flowing from a body wound or incision may be set in motion by an osmotic pressure type phenomenon supplemented by gravity acting in conjunction with the capillary movement through the absorbent material. The simplest path for the moving fluids contained within the bandage is the path of evaporation.

FIG. 5 shows the bandage of the present invention in place on the upper arm of a person in a supine position. The bandage is draped so that the nonabsorptive portion is pointed downward toward the ground.

EXAMPLE 1

An initial comparative test was run to establish the efficacy of the evaporating bandage of the present invention. In order to simulate body fluids, 5 ounces of non-dairy creamer were dissolved in 10 ounces of coffee, having a temperature of about 98.6° F. The resultant solution possessed a viscosity within the range of human blood. The solution was gradually dispensed through an eye dropper (to simulate body fluids oozing from injured skin) onto a bandage having an absorbent layer of spun cotton positioned to overlap and in a staggered relationship with a second layer of nylon. The solution was applied to the top edge of the spun cotton layer. A control bandage of spun cotton having the same dimensions was prepared and saturated. Evaporation of the fluid contained by the bandage of the present invention in the experiment was seven times faster than found in the cotton bandage of the prior art.

EXAMPLE 2

Another comparative test was run to establish the efficacy of the evaporating bandage of the present invention. In order to simulate body fluids, a mixture of three tablespoons of non-dairy creamer were dissolved in eight ounces of coffee, having a temperature of about 98.6° F. The resultant solution possessed a viscosity substantially greater than the viscosity range of human blood. A test bandage (A) comprising an evaporating bandage of the present invention measuring 3¼ inches by 2¾ inches by 3/16 inch was fabricated using a sterilized terry cloth and a ribbed nylon strip fastened thereto in such a manner that the terry cloth strip and nylon strip were in staggered, contacting relationship with each other. The sample was mounted on a test stand in a vertical position. A control bandage (B) made of a standard gauze material, measuring 3¼ inches by 2¾ inches by 3/16 inch, was similarly mounted on the test stand. Using a medicine dropper that dispenses drops equal to 1/16 of a milliliter, one drop of liquid was applied to the top edge of test bandage A and control B every three seconds. After 8.75 ml, the control bandage became saturated and could no longer contain the liquid being applied and, thereafter, evidenced considerable leakage therefrom when further liquid was applied.

In contrast, the evaporating test bandage of the present invention held 25 ml without evidencing any leakage. The test demonstrates the greater ability of the evaporating bandage of the present invention compared with the prior art, to contain profuse oozing of body fluids when in place over an incision, wound or burn. This greater containment capacity will decrease the frequency of bandage changes in those situations where the skin is severely injured.

EXAMPLE 3

A comparative test was run wherein 2.5 ml of tap water was applied at room temperature to an evaporating bandage test sample which measured 3¼ inches by 2¼ inches by ⅛ inch and also to a control gauze bandage having the same dimensions. Both bandages were mounted in a vertical position. The tap water was applied to the top edges of the test and control bandages at the rate of one drop every three seconds. The evaporative test bandage was dry to the touch 25 minutes after the 2.5 ml of water was supplied. The control sample bandage was dry 135 minutes after the 2.5 ml of water was applied.

EXAMPLE 4

This test was conducted using samples having the identical dimensions, along with test amounts and procedures as set forth in Example 3 above; however, both the test and control bandages were inclined at an angle of approximately 30° from vertical to simulate bandages draped on the human body so that a portion of the bandage will tilt at an angle and be pointing toward the ground. The test stand containing the samples was placed in a room having a temperature of 71° F. with no air movement. Test B was dry 65 minutes after the 2.5 ml of water was applied. The control sample B was not dry until 155 minutes after the 2.5 ml of water was applied.

EXAMPLE 5

The procedure used in Example 3 above was duplicated with the exception that the control sample placed in a horizontal position, i.e., perpendicular to the vertical plane. The water was applied to one edge of the sample. The control bandage was not dry until 220 minutes after the 2.5 ml of water was applied. This test is closer to the realistic occurrences when gauze bandaging is applied to a person who is bedridden, as the bandaging would be lying flat upon the skin of the patient.

In the foregoing specification, the presently preferred embodiments of the invention are described; however, it will be understood that the invention can be otherwise embodied within the scope of the following claims.

I claim:

1. A method of containing fluids emanating from the human body using an evaporative bandage, comprising contacting the location on the body from which said fluids are emanating with a bandage, said bandage comprising a first layer made of a moisture-absorbent material and a second layer made of a non-moisture absorbent material; said first and second layers having top and bottom edge portions which are aligned and secured in staggered positions relative to each other so that at one end, said first layer top edge portion extends beyond the second layer top edge portion thereof and is in contact with the location on the body from which said fluids are emanating, and, correspondingly, said second layer bottom edge portion extends beyond the said first layer bottom edge portion at the other end thereof, there being a resulting area wherein a portion of the surface of the lower portion of said first layer is in direct contact with a portion of the surface of the upper portion of said second layer.

2. The method in claim 1 wherein the first layer is made of a moisture-absorbent material comprising cotton.

3. The method defined in claim 1 wherein the second layer is made of a non-moisture-absorbent material comprising a polyamide.

4. The method defined in claim 1 wherein the first layer sleeve is made of a moisture-absorbent material comprising wool.

5. The method defined in claim 1 wherein the first layer sleeve is made of a moisture-absorbent material comprising cotton and the second layer is made of a non-moisture-absorbent material comprising a polyamide.

6. The method defined in claim 2 wherein said cotton is terry cloth.

7. The method defined in claim 2 wherein said cotton comprises a first section made of terry cloth secured to a second section made of gauze.

8. The method of claim 6 wherein said non-moisture absorbent material comprises a polyamide material.

9. The method of claim 7 wherein said non-moisture absorbent material comprises a polyamide material.

* * * * *